US010632079B2

(12) United States Patent
Hiraoka

(10) Patent No.: US 10,632,079 B2
(45) Date of Patent: Apr. 28, 2020

(54) MICROSPHERES HAVING CORE/SHELL STRUCTURE

(75) Inventor: Shogo Hiraoka, Osaka (JP)

(73) Assignee: Otsuka Pharmaceuticals Co., Ltd., Tokyo (JP)

(*) Notice: Subject to any disclaimer, the term of this patent is extended or adjusted under 35 U.S.C. 154(b) by 528 days.

(21) Appl. No.: 12/666,761

(22) PCT Filed: Jun. 9, 2008

(86) PCT No.: PCT/JP2008/060919
§ 371 (c)(1),
(2), (4) Date: Mar. 24, 2010

(87) PCT Pub. No.: WO2009/001697
PCT Pub. Date: Dec. 31, 2008

(65) Prior Publication Data
US 2010/0203151 A1    Aug. 12, 2010

(30) Foreign Application Priority Data
Jun. 25, 2007    (JP) .................................. 2007-166183

(51) Int. Cl.
*A61K 9/58*    (2006.01)
*A61K 31/496*    (2006.01)
*A61K 9/50*    (2006.01)
*A61K 9/00*    (2006.01)

(52) U.S. Cl.
CPC .......... *A61K 9/5031* (2013.01); *A61K 9/5089* (2013.01); *A61K 31/496* (2013.01); *A61K 9/0024* (2013.01)

(58) Field of Classification Search
CPC .. A61K 9/5031; A61K 9/5005; A61K 9/0024; A61K 31/496
See application file for complete search history.

(56) References Cited

U.S. PATENT DOCUMENTS 4,568,559 A * 2/1986 Nuwayser ............ A61K 9/1647
424/493
5,654,008 A * 8/1997 Herbert ................ A61K 9/1647
264/4.1

(Continued)

FOREIGN PATENT DOCUMENTS

EP    0 669 128 A1    8/1995
EP    1330249 B1 *    9/2002

(Continued)

OTHER PUBLICATIONS

Graves et al., International Journal of Pharmaceutics, 270: 251-262 (2004).*

(Continued)

*Primary Examiner* — Lakshmi S Channavajjala
(74) *Attorney, Agent, or Firm* — Finnegan, Henderson, Farabow, Garrett & Dunner, LLP

(57) ABSTRACT

Disclosed are microspheres having a core/shell structure and a spherical shape, wherein (a) the core comprises solid-state aripiprazole, and (b) the shell coats all or most of the surface of the core, and the shell comprises a biodegradable polymer; a process for producing the microspheres; and an injectable aqueous suspension formulation containing the microspheres; and the like.

11 Claims, 7 Drawing Sheets

100 μm

(56) References Cited

U.S. PATENT DOCUMENTS

| | | | |
|---|---|---|---|
| 5,656,299 A * | 8/1997 | Kino | A61K 9/1647 424/426 |
| 5,770,231 A | 6/1998 | Mesens et al. | |
| 6,358,443 B1 * | 3/2002 | Herbert | A61K 9/1694 264/13 |
| 7,157,102 B1 * | 1/2007 | Nuwayser | A61K 9/167 424/452 |
| 2004/0247870 A1 | 12/2004 | Brown et al. | |
| 2005/0032811 A1 * | 2/2005 | Brown | A61K 9/0019 514/253.07 |
| 2005/0032836 A1 * | 2/2005 | Greco | C07D 211/52 514/317 |
| 2005/0148597 A1 * | 7/2005 | Kostanski et al. | 514/253.07 |
| 2006/0096715 A1 | 5/2006 | Suzuki et al. | |

FOREIGN PATENT DOCUMENTS

| | | |
|---|---|---|
| EP | 1675573 B2 * | 10/2008 |
| JP | 8-151321 A | 6/1996 |
| JP | 2000-239152 A | 9/2000 |
| WO | 94-10982 A1 | 11/1993 |
| WO | 01/83594 A1 | 11/2001 |
| WO | 2005/016262 A2 | 2/2005 |
| WO | 2008/041245 A2 | 4/2008 |

OTHER PUBLICATIONS

Expert Consensus Guideline Series, Optimizing Pharmacologic Treatment of Psychotic Disorders, Journal of Clinical Psychiatry, 64 (suppl 12) (2003) pp. 1-31.*

Nahata et al. D-optimizing designing and optimization of long acting microsphere based injectable formualtion of aripiprazole. Drug Development and Industrial Pharmacy. 2008, 34:668-675.*

Layre et al. Nanoencapsulation of a crystalline drug. Pharmaceutical Nanotechnology. International Journal of Pharamceutics. 2005, vol. 298, 323-327.*

Office Action dated Dec. 2, 2011 on Russian Patent Application No. 2009 145299.

Aliphatic Compounds, Handbook of Pharmaceutical Excipients, 5th Ed., Pharmaceutical Press and American Pharmacists Association (Date of Revision: Aug. 26, 2005).

* cited by examiner

100μm 5.00μm 20.0μm 20.0μm 5.00 μm 10.0 μm 4.00μm 20.0μm

100 μm 10.0 μm 20.0 μm 4.00 μm

MICROSPHERES HAVING CORE/SHELL STRUCTURE

TECHNICAL FIELD

The present invention relates to microspheres containing aripiprazole, a process for producing the same, and an injectable aqueous suspension formulation containing the microspheres.

BACKGROUND ART

For the controlled release of drugs such as aripiprazole, microspheres composed of a drug and a base polymer are used. Various conventionally known microspheres are of the matrix type in which a drug is substantially uniformly distributed in a base matrix such as a polymer.

For example, base/drug matrix-type microparticles are obtained by dissolving a base and a drug together in a solvent, drying the solution as such, followed by compression and fragmentation (Patent Document 1). However, when such a matrix-type microsphere has a high drug content, e.g., a weight ratio of drug to base of 1 or more (i.e., a drug content of 50% by weight or more), the drug constitutes a large part of the microsphere. Consequently, a large amount of the drug also exists on the surface of the microsphere. It is generally considered that a large amount of the drug present on the surface of the microsphere disables control of release by the base.

According to another known process, a drug and a base are dissolved in an organic solvent such as dichloromethane, an O/W emulsion is prepared in an aqueous system, and dichloromethane is vaporized (Patent Document 2).
[Patent Document 1] US 2004/0247870 A1
[Patent Document 2] WO 94/10982

DISCLOSURE OF THE INVENTION

Problem to be Solved by the Invention

According to the research conducted by the inventor, when the process disclosed in Patent Document 2 is employed with a high drug content, particularly with a high aripiprazole content, drug crystal growth occurs in the emulsion, resulting in the production of particles that are not spherical, but the particles take a shape derived from the drug crystal (e.g., needle or rhomboid). Consequently, the process fails to produce microspheres having a spherical shape and a core/shell structure (see later-described Comparative Examples 1 and 2).

Considering flowability during filling in production of an injectable formulation, ability to pass through a syringe (syringeability) during administration of an injectable formulation, intramuscular stimulation, etc., it is preferable that microspheres have a spherical shape.

Moreover, since aripiprazole should be administered at a high dose, an injectable suspension formulation to be administered contains an increased amount of particles. The increased amount of particles contained in the injectable formulation raises the viscosity of the suspension, causing lower syringeability during administration. Accordingly, it is desired that the proportion of a base such as a polymer in the microsphere be reduced as much as possible so that the microsphere contains a large amount of aripiprazole which is an active ingredient.

The present invention aims to provide microspheres having a high aripiprazole content, a process for producing the same, and an injectable aqueous suspension formulation containing the microspheres.

Means for Solving the Problem

The present inventors conducted intensive research to solve the above problems and achieved the following findings.

(a) When aripiprazole and a biocompatible polymer are dissolved in an organic solvent, the resulting solution is mixed with water in the presence or absence of an emulsifier to form an emulsion, under conditions that suppress evaporation of the organic solvent, and then the organic solvent is removed at least partially from the emulsion, under conditions that allow the aripiprazole to precipitate in the form of spherical particles in the emulsion; surprisingly, spherical microspheres having a core/shell structure in which the biocompatible polymer coats all or most of the surface of the aripiprazole particle are produced.

(b) The microspheres with a core/shell structure obtained in this way have a high aripiprazole content.

(c) The microspheres with a core/shell structure and a high aripiprazole content have excellent sustained-release properties.

As a result of further research based on these findings, the present invention has been accomplished. The present invention provides microspheres having a core/shell structure and a high aripiprazole content, a process for producing the same, an injectable aqueous suspension formulation containing the microspheres, etc. as shown in the following Items 1 to 20.

Item 1. Microspheres having a core/shell structure and a spherical shape,
(a) the core comprising solid-state aripiprazole; and
(b) the shell coating all or most of the surface of the core, and the shell comprising a biodegradable polymer.

Item 2. Microspheres according to Item 1, wherein the aripiprazole content is 55 to 95% by weight of the total weight of the microsphere.

Item 3. Microspheres according to Item 1 or 2, having a mean particle size of 20 to 150 μm.

Item 4. Microspheres according to any one of Items 1 to 3, wherein the shell has an average thickness of 0.5 to 20 μm.

Item 5. Microspheres according to any of Items 1 to 4, wherein the biodegradable polymer is at least one member selected from the group consisting of polylactic acids and lactic acid-glycolic acid copolymers.

Item 6. Microspheres according to Item 5, wherein the polylactic acids or the lactic acid-glycolic acid copolymers have a molecular weight of 5000 to 200000.

Item 7. An injectable aqueous suspension formulation comprising the microspheres according to any one of Items 1 to 6, a vehicle therefor, and water for injection.

Item 8. An injectable aqueous suspension formulation according to Item 7, which upon injection releases aripiprazole over a period of at least one month.

Item 9. An injectable aqueous suspension formulation according to Item 7 or 8, wherein the vehicle comprises:
(1) one or more suspending agents,
(2) one or more isotonic agents, and
(3) optionally one or more pH adjusting agents.

Item 10. A process for producing microspheres having a core/shell structure and a spherical shape (particularly microspheres according to Item 1) comprising:

(i) preparing a solution containing aripiprazole, a biodegradable polymer, and an organic solvent;
(ii) mixing the solution obtained in step (i) with water to obtain an O/W emulsion, under conditions that suppress evaporation of the organic solvent; and
(iii) removing the organic solvent at least partially from the O/W emulsion under conditions effective for allowing precipitation of spherical particles of the aripiprazole.

Item 11. A process according to Item 10, wherein the organic solvent used in step (i) is a water-immiscible organic solvent.

Item 12. A process according to Item 10 or 11, wherein the water used in step (ii) contains an emulsifier.

Item 13. A process according to any of Items 10 to 12, wherein step (ii) comprises the substeps of (a) dispersing the solution obtained in step (i) in water in the presence or absence of an emulsifier to form an O/W emulsion and (b) dispersing the O/W emulsion obtained in substep (a) in water in the presence or absence of an emulsifier to form an O/W emulsion.

Item 14. A process according to any of Items 10 to 13, wherein, in step (ii), the O/W emulsion is produced under low-temperature conditions effective for suppressing evaporation of the organic solvent, and in step (iii), the low temperature emulsion obtained in step (ii) is stirred in an open system at room temperature to allow the organic solvent to volatilize.

Item 15. A method for treating schizophrenia, comprising administering an injectable aqueous suspension formulation according to any one of Items 7 to 9 to a patient in need of such treatment.

Item 16. Use of an injectable aqueous suspension formulation according to any of Items 7 to 9 for production of a medicament for treating schizophrenia.

Item 17. An injectable aqueous suspension formulation according to any of Items 7 to 9 for use in treating schizophrenia.

Item 18. A method for treating schizophrenia, comprising administering microspheres according to any one of Items 1 to 6 to a patient in need of such treatment.

Item 19. Use of microspheres according to any one of Items 1 to 6 for production of a medicament for treating schizophrenia.

Item 20. Microspheres according to any of Items 1 to 6 for use in treating schizophrenia.

Effects of the Invention (a) The microspheres having a core/shell structure of the present invention have excellent sustained-release properties, since all or most of the surface of the core containing aripiprazole are coated with a shell made of a biodegradable polymer.

(b) Further, since the microspheres are spherical, they have excellent flowability during filling in the production of injectable aqueous suspension formulation and excellent ability to pass through a syringe (syringeability) during administration of the injectable aqueous suspension formulation.

(c) Moreover, since the microspheres have a high aripiprazole content, administration of even a small amount of particles (microspheres) in an injectable formulation allows for the administration of a high dose of aripiprazole.

(d) Since the microspheres are spherical, when they are used in an injectable formulation, caking (formation of a hard layer by sedimented particles) after suspension is less likely to occur. Therefore, the microshperes are easily redispersed even when they are sedimented after being dispersed in the injectable formulation.

(e) Since aripiprazole and a biodegradable polymer are dissolved once in an organic solvent during production of the microspheres of the present invention, filter sterilization is possible and no sterile active ingredient is required; thus, there are great advantages in the production.

BEST MODE FOR CARRYING OUT THE INVENTION

Microspheres Having a Core/Shell Structure

Figure 1:
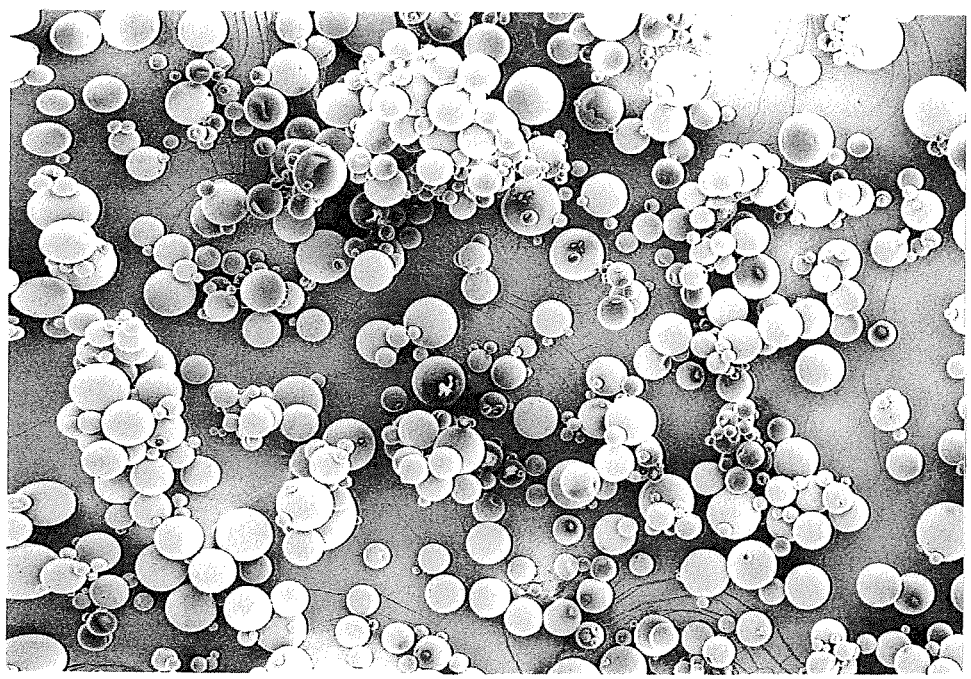
FIG. 1 is an electron microscope image of the microspheres obtained in Example 5.

The microspheres having a core/shell structure of the present invention are spherical, as shown in the electron microscope images (FIGS. 1 and 2) of microspheres obtained in Examples below.

As shown in the electron microscope images (FIGS. 4-7) of microspheres obtained in Examples below, the microsphere having a core/shell structure basically comprises a core constituting a central nucleus and a shell that coats all or most of the surface of the core.

The mean particle size of the microspheres is about 20 to 150 μm, and preferably about 30 to 100 μm.

In the present specification, the mean particle size of the microspheres is measured by the method that will be described in Examples below.

The microspheres of the invention have excellent sustained-release properties.

Core

The core basically contains solid-state aripiprazole, has a spherical shape and forms a central nucleus of the microsphere having a core/shell structure of the invention (see FIGS. 4-7).

Usually, the core consists essentially of solid-state aripiprazole, but may additionally contain a biodegradable polymer that will be described below. Therefore, the core basically consists essentially of aripiprazole or a mixture of aripiprazole and a biodegradable polymer. Moreover, when an emulsifier is used during production as will be described later, the core may further contain the emulsifier occasionally.

The amount of aripiprazole contained in the core is very high relative to the total weight of the microsphere. Generally, the aripiprazole content is about 55 to 95% by weight, preferably about 60 to 90% by weight, and more preferably about 60 to 80% by weight, relative to the total weight of the microsphere.

The aripiprazole content of the whole microsphere is measured by the method that will be described in Examples below.

The form of the solid-state aripiprazole contained in the core is not limited as long as it is solid, but generally it is an amorphous solid (especially a spherical non-crystalline solid). In some cases, aripiprazole may exist in the form of an aggregate of many fine particles (primary particles), a crystal, etc. Aripiprazole in such forms preferably has a spherical shape.

Shell

The shell basically coats the entire surface of the above core (refer to FIGS. 4-7). However, in some cases, the shell may coat most of the surface of the core, e.g., about 80 to 90% of the surface of the core, and the core may be partially exposed.

The shell consists essentially of a biodegradable polymer. The shell may additionally contain a small amount of the above aripiprazole. Thus, the shell basically consists essentially of a biodegradable polymer or a mixture of aripiprazole and a biodegradable polymer. Moreover, when an emulsifier is used during production as will be described later, the shell may further contain the emulsifier occasionally.

Typically, however, the shell of the microsphere of the present invention is made mostly of a biodegradable polymer (i.e., consists essentially of a biodegradable polymer), while the core is made mostly of aripiprazole (i.e., consists essentially of aripiprazole).

The average thickness of the shell may be suitably adjusted so that the amount of aripiprazole contained in the core is about 55 to 95% by weight, preferably about 60 to 90% by weight, and more preferably 60 to 80% by weight, relative to the total weight of the microsphere, and so that the desired sustained-release properties are acquired. For example, the average thickness is about 0.5 to 20 μm, preferably about 1 to 10 μm, and more preferably about 1 to 5 μm. In each of FIGS. 4 to 7, the distance between the two triangles (▲) indicates the thickness of the shell. The average thickness of the shell is a value measured by the method that will be described in Examples below.

Any biodegradable polymers may be used to form the shell as long as they are gradually decomposed in the body to provide the desired sustained-release properties. Examples of biodegradable polymers include polylactic acids, polyglycolic acids, lactic acid-glycolic acid copolymers, polycitric acids, polymalic acids, lactic acid-aspartic acid copolymers, lactic acid-hydroxycaproic acid copolymers, glycolic acid-hydroxycaproic acid copolymers, polypropiolactones, polybutyrolactones, polyvalerolactones, polycaprolactones, polytrimethylene carbonates, poly(p-dioxanone)s, poly(α-cyanoacrylic acid ester)s, poly(β-hydroxybutyric acid)s, polytrimethylene oxalates, polyorthoesters, polyorthocarbonates, polyethylene carbonates, poly-γ-benzyl-L-glutamic acids, poly(L-alanine)s and polyalginic acids, polycarbonates, polyester amides, poly(amino acid)s, poly(alkylene alkylate)s, polyethylene glycols, polyurethanes, and like homopolymers, and copolymers thereof. Among them, polylactic acids and lactic acid/glycolic acid copolymers are preferred. These biodegradable polymers for forming shells may be used singly or in a combination of two or more.

When polylactic acids or lactic acid-glycolic acid copolymers are used, the molecular weight thereof may be suitably selected from a wide range, e.g., about 5000 to 200000, preferably about 20000 to 150000, and more preferably about 50000 to 120000.

The above molecular weight herein is the polystyrene-equivalent number average molecular weight measured by gel permeation chromatography (GPC) using polystyrene as the standard.

The ratio of lactic acid to glycolic acid (lactide:glycolide) in the lactic acid-glycolic acid copolymers is not limited and may be suitably selected from a wide range. Generally, the molar ratio of lactic acid to glycolic acid (lactide:glycolide) is about 99:1 to 50:50, and preferably about 99:1 to 75:25.

Suitable polylactic acids may be any of poly(D-lactic acid), poly(L-lactic acid), and poly(DL-lactic acid), and poly(DL-lactic acid) is preferred. Suitable lactic acid-glycolic acid copolymers may be any of D-lactic acid-glycolic acid copolymers, L-lactic acid-glycolic acid copolymers, and DL-lactic acid-glycolic acid copolymers, and DL-lactic acid-glycolic acid copolymers are preferred.

In addition to the above biodegradable polymers, the shell may optionally contain nondegradable biocompatible polymers.

Production Process

The process for producing the microspheres having a core/shell structure of the present invention comprises the steps of:
 (i) preparing a solution containing aripiprazole, a biodegradable polymer, and an organic solvent;
 (ii) mixing the solution obtained in step (i) with water to obtain an oil-in-water (O/W) emulsion under conditions that suppress evaporation of the organic solvent; and
 (iii) removing the organic solvent at least partially from the O/W emulsion under conditions effective for allowing precipitation of spherical particles of the aripiprazole.

Step (i)

First, aripiprazole and a biodegradable polymer are dissolved in an organic solvent to obtain a homogeneous solution.

The crystal form of the aripiprazole is not limited. Usable are a monohydrate form (aripiprazole hydrate A) or various anhydrous forms known to exist in the forms of anhydrous crystal B, anhydrous crystal C, anhydrous crystal D, anhydrous crystal E, anhydrous crystal F, anhydrous crystal G, and the like. These crystal forms may be used singly or in a combination of two or more.

The organic solvent is not limited as long as it can dissolve aripiprazole and biodegradable polymers.

Examples of such organic solvents include chloroform, dichloroethane, trichloroethane, dichloromethane, carbon tetrachloride, and like halogenated hydrocarbons; ethyl ether, isopropyl ether, and like ethers; ethyl acetate, butyl acetate, and like fatty acid esters; benzene, toluene, xylene, and like aromatic hydrocarbons; ethanol, methanol, isopropanol, and like alcohols; acetonitrile and like nitriles; dimethylformamide and like amides; and mixtures thereof, etc. Among them, water-immiscible organic solvents, especially dichloromethane, are preferred.

The concentration of aripiprazole relative to the organic solvent is usually about 0.1 to 20% (W/V), preferably about 1 to 10% (W/V), and more preferably about 3 to 7% (W/V). The "% (W/V)" as the unit of the concentration of aripiprazole denotes the percentage of the weight of aripiprazole relative to the volume of the organic solvent. For example, 1 g of aripiprazole in 100 ml of the organic solvent is expressed as 1% (W/V).

The concentration of the biodegradable polymer relative to the organic solvent is usually about 0.1 to 10% (W/V), preferably about 0.5 to 5% (W/V), and more preferably about 1 to 3% (W/V).

The amount of biodegradable polymer used may be suitably adjusted so that the aripiprazole content of the core is about 55 to 95% by weight, preferably about 60 to 90% by weight, and more preferably 60 to 80% by weight, relative to the total weight of the microsphere; and so that the desired sustained-release properties are obtained.

Step (ii)

Next, the solution (containing the aripiprazole, biodegradable polymer, and organic solvent) obtained in step (i) is mixed with water to obtain an O/W emulsion in which the solution is uniformly dispersed in the water.

When the organic solvent used in step (i) is water-immiscible, the solution obtained in step (i) is hardly miscible with water and is therefore dispersed in water in the form of small droplets.

When a water-miscible solvent is used in step (i), the solution obtained in step (i) is dispersed as micelles by using an emulsifier.

The proportion of the solution obtained in step (i) relative to the water is not limited as long as an O/W emulsion with a desired particle size may be formed. Usually, the amount of the solution relative to the water is about 0.1 to 20% by weight, preferably about 0.5 to 10% by weight, and more preferably about 1 to 5% by weight.

Irrespective of whether the organic solvent used in step (i) is water-miscible or water-immiscible, an emulsifier may be added to the water.

Any emulsifiers may be used as long as they can form an O/W emulsion, preferably a stable O/W emulsion. Examples of such emulsifiers include sodium oleate, sodium stearate, sodium lauryl sulfate, and like anionic surfactants; polyoxyethylene sorbitan fatty acid esters, polyoxyethylene castor oil derivatives, and like nonionic surfactants; polyvinyl pyrrolidone, polyvinyl alcohol, carboxymethylcellulose, lecithin, gelatin, hyaluronic acid, and the like. These emulsifiers may be used singly or in a combination of two or more.

When using an emulsifier, the concentration is not limited and may be selected from a wide range, e.g., about 0.0001 to 20% by weight, preferably about 0.001 to 10% by weight, and more preferably about 0.001 to 5% by weight, relative to the amount of water.

The O/W emulsion is formed under temperature conditions that do not allow freezing of the organic solvent and water and that suppress evaporation of the organic solvent. A suitable temperature depends on the type of the organic solvent. For example, in the case of using dichloromethane as the organic solvent, the temperature is, under atmospheric pressure, typically about 0 to 18° C., and preferably about 0 to 15° C.

The method of preparing an O/W emulsion is not limited, and any method in which the above solution (containing the aripiprazole, biodegradable polymer, and organic solvent) is dispersed in water as suitable-sized droplets or micelles can be used. For example, an O/W emulsion may be prepared by stirring a mixture of the above solution and water using a homogenizer or the like at a suitable rotational speed to fragment the solution in the water, or by passing a mixture of the above solution and water through a filter with small through-pores such as a ceramic filter at a fixed speed to fragment the solution, or by passing the above solution through a filter with small through-pores such as a ceramic filter at a fixed speed to fragment the solution and then mixing the fragmented solution with water.

If necessary, the formation of an emulsion in step (ii) may be carried out in multiple substeps. For example, when step (ii) is carried out in two substeps, in substep (a), the solution obtained in step (i) is dispersed in water in the presence or absence of an emulsifier to form an O/W emulsion, and in substep (b), the resulting O/W emulsion is further dispersed in water in the presence or absence of an emulsifier to form an O/W emulsion. Moreover, if necessary, step (ii) may be performed in three or more substeps including these two substeps.

In the case of forming an O/W emulsion in multiple substeps like this, the proportion of the solution obtained in step (i) relative to the total amount of the water used in the substeps is not limited as long as an O/W emulsion with a desired particle size can be obtained, and is usually about 0.1 to 20 weight %, preferably about 0.5 to 10 weight %, more preferably about 1 to 5 weight %. The aforementioned emulsifier may be used as the emulsifier in each substep.

The concentration of the emulsifier in each substep is not particularly limited and may be selected from a wide range. The concentration is typically about 0.0001 to 20 weight %, preferably about 0.001 to 10 weight %, more preferably about 0.001 to 5 weight %, based on the amount of water.

When step (ii) is carried out in such multiple substeps, each substep is conducted under temperature conditions in which the organic solvent and water do not freeze and evaporation of the organic solvent is suppressed. A suitable temperature depends on the type of the organic solvent. For example, in the case of using dichloromethane as the organic solvent, the temperature is, under atmospheric pressure, typically about 0 to 18° C., and preferably about 0 to 15° C.

The size of the droplets or micelles in the O/W emulsion obtained in step (ii) can be adjusted using various methods. For example, the size can be reduced by carrying out high speed processing with the above homogenizer or the like, or by passing them through a filter with a small pore size. The size of the droplets or micelles can be increased by increasing the contents of the aripiprazole and biodegradable polymer in the above organic solvent.

When the size of the droplets or micelles is reduced to obtain microspheres with a smaller particle size, a larger specific surface area increases the required amount of shell material, making the shell thinner. An increased proportion of biodegradable polymer in the droplets or micelles makes the shell thicker. The size of the core may be adjusted by suitably adjusting the aripiprazole content in the solution, the size of the droplets or micelles in the emulsion (the size of microspheres) and the like.

Step (iii)

Removal of the organic solvent at least partially from the O/W emulsion obtained in step (ii) gives an aqueous suspension of microspheres having a core/shell structure in which all or most of the surface of aripiprazole are coated with a biodegradable polymer.

The organic solvent can be at least partially removed by various methods, for example, by heating the above emulsion under atmospheric pressure, or by leaving the emulsion at room temperature. In these methods, the boiling point of the organic solvent used is preferably lower than the boiling point of water.

In step (iii), it is important to carry out removal of at least a portion of the organic solvent from the O/W emulsion under conditions that are effective for allowing aripiprazole to precipitate in the form of spherical particles.

The conditions effective for allowing precipitation of spherical particles of the aripiprazole may be achieved by removing at least a portion of the organic solvent by allowing the organic solvent to gradually volatilize. It is presumed that, by gradually removing at least a portion of the organic solvent in this way, aripiprazole present at a higher concentration in each droplet is preferentially precipitated as a spherical particle, and then the biodegradable polymer is deposited on the surface of the spherical particle of aripiprazole, whereby the core/shell structure of the microsphere is thus formed.

A typical way of allowing the organic solvent to gradually volatilize is stirring the low-temperature O/W emulsion obtained in step (ii) at atmospheric pressure and at room temperature so that the O/W emulsion is allowed to come to room temperature to thereby allow at least a portion of the organic solvent to gradually volatilize.

Rapid removal of the organic solvent from the O/W emulsion in step (iii) causes the aripiprazole and the biodegradable polymer to simultaneously precipitate, thereby forming a matrix of the aripiprazole and the biodegradable polymers, or causes aripiprazole crystals to grow.

In step (iii), the organic solvent is removed until the microspheres of the present invention are produced. For example, under atmospheric pressure, the stirring is carried out typically for 1 to 24 hours, preferably 2 to 12 hours, in the case of using dichloromethane as the organic solvent.

Note that, step (ii) and step (iii) may be performed as a series of steps. For example, in step (ii), the organic solvent solution obtained in step (i) is mixed with water under conditions that suppress evaporation of the solvent (generally, at a low temperature) to obtain a low-temperature O/W emulsion in which the solvent is evenly dispersed; however, it is not necessary to ensure the evenness of the O/W emulsion, and the stirring at room temperature may be started with an emulsion which is not sufficiently even. In this case, the volatilization of the organic solvent and the formation of an even emulsion proceed simultaneously.

Since the microspheres obtained in step (iii) are present in water, they can be isolated by separating the microspheres using a suitable method such as filtration, and then the obtained microspheres are subjected to air-drying, drying under reduced pressure, lyophilization, or the like. The dried microspheres may be sieved as necessary, to have a desired mean particle size.

In the production process of the present invention, since the aripiprazole and the biodegradable polymer are dissolved once in an organic solvent in step (i) above, filter sterilization is possible, allowing the use of a non-sterile bulk aripiprazole powder. Thus, there are great advantages in the production process.

Injectable Aqueous Suspension Formulation

The microspheres having a core/shell structure of the invention have excellent sustained-release properties, as is clear from Test Examples below. Further, since the microspheres are spherical, they have excellent flowability during filling in the production of an injectable formulation, and excellent syringeability during administration of an injectable formulation. Moreover, since the microspheres have a high aripiprazole content, administration of a small amount of particles (microspheres of the present invention) in an injectable formulation allows for the administration of a high dose of aripiprazole.

Therefore, the present invention provides a method for treating schizophrenia, comprising administering microspheres of the present invention to a patient in need of such treatment. The present invention also provides use of the microspheres of the present invention for production of a medicament for treating schizophrenia. The present invention further provides the microspheres for use in the treatment of schizophrenia.

Further, the microspheres having a core/shell structure of the invention can be suitably used in an injectable aqueous suspension formulation.

The injectable aqueous suspension formulation of the present invention contains the microspheres of the invention, a vehicle therefor, and water for injection.

The amount of the microspheres in the injectable aqueous suspension formulation is not limited as long as the microspheres are dispersed in the injectable formulation. For example, the microsphere content of the injectable formulation is about 5 to 50% by weight, preferably about 10 to 40% by weight, and more preferably about 10 to 30% by weight.

The vehicle contained in the injectable aqueous suspension formulation of the invention contains:
(a) at least one suspending agent,
(b) at least one isotonic agent, and
(c) optionally at least one pH adjusting agent.

(a) Suspending Agent

Examples of suspending agents contained in the injectable aqueous suspension formulation include sodium carboxymethyl cellulose, hydroxypropyl cellulose, carboxymethyl cellulose, hydroxypropylethyl cellulose, hydroxypropylmethyl cellulose, polyvinylpyrrolidone, and the like.

Examples of other suspending agents suitable for use in the vehicle for the microspheres of the invention include various polymers, low molecular weight oligomers, natural products, and surfactants (including nonionic and ionic surfactants), such as cetylpyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., commercially available Tweens (Registered trademark) such as Tween 20 (Registered trademark) and Tween 80 (Registered trademark) (ICI Specialty Chemicals)); polyethylene glycols (e.g., Carbowaxs 3350 (Registered trademark) and 1450 (Registered trademark), and Carbopol 934 (Registered trademark) (Union Carbide)), dodecyl trimethyl ammonium bromide, polyoxyethylene stearates, colloidal silicon dioxide, phosphates, sodium dodecyl sulfate, carboxymethylcellulose calcium, hydroxypropyl celluloses (e.g., HPC, HPC-SL, and HPC-L), methylcellulose, hydroxyethylcellulose, hydroxypropylmethylcellulose, hydroxypropylmethyl-cellulose phthalate, non-crystalline cellulose, magnesium aluminium silicate, triethanolamine, polyvinyl alcohol (PVA), 4-(1,1,3,3-tetramethylbutyl)-phenol polymers with ethylene oxide and formaldehyde (also known as tyloxapol, superione, and triton), poloxamers (e.g., Pluronics F68 (Registered trademark) and F108 (Registered trademark), which are block copolymers of ethylene oxide and propylene oxide); poloxamines (e.g., Tetronic 908 (Registered trademark), also known as Poloxamine 908 (Registered trademark), which is a tetrafunctional block copolymer derived from the sequential addition of propylene oxide and ethylene oxide to ethylenediamine (BASF Wyandotte Corporation, Parsippany, N.J.)); a charged phospholipid such as dimyristoyl phosphatidylglycerol, dioctylsulfosuccinate (DOSS); Tetronic 1508 (Registered trademark) (T-1508) (BASF Wyandotte Corporation), dialkyl esters of sodium sulfosuccinic acid (e.g., Aerosol OT (Registered trademark), which is a dioctyl ester of sodium sulfosuccinic acid (American Cyanamid)); Duponol P (Registered trademark), which is a sodium lauryl sulfate (DuPont); Tritons X-200 (Registered trademark), which is an alkyl aryl polyether sulfonate (Rohm and Haas); Crodestas F-110 (Registered trademark), which is a mixture of sucrose stearate and sucrose distearate (Croda Inc.); p-isononylphenoxypoly-(glycidol), also known as Olin-10G (Registered trademark) or Surfactant 10-G (Registered trademark) (Olin Chemicals, Stamford, Conn.); Crodestas SL-40 (Registered trademark) (Croda, Inc.); and SA9OHCO, which is $C_{18}H_{37}CH_2(CON(CH_3))$—$CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-nonyl β-D-glucopyranoside; octanoyl-N-methylglucamide; n-octyl-β-D-glucopyranoside; octyl β-D-thioglucopyranoside; and the like.

Most of these suspending agents are known pharmacological excipients and are described in detail, for example, in the Handbook of Pharmaceutical Excipients, published jointly by the American Pharmaceutical Association and The Pharmaceutical Society of Great Britain (The Pharmaceutical Press, 1986).

These suspending agents are commercially available and can be produced by techniques known in the art. These suspending agents may be used singly or in a combination of two or more.

The amount of suspending agent is not limited as long as it is acceptable for use in an injectable formulation, and may be adjusted to an amount sufficient for suspending the microspheres of the invention in the injectable aqueous suspension formulation. The amount is typically 0.01 to 20 parts by weight, preferably 0.1 to 10 parts by weight, per 100 parts by weight of water for injection contained in the injectable formulation of the invention.

(b) Isotonic Agent

The isotonic agent contained in the injectable aqueous suspension formulation of the invention is not limited as long as it can make the injectable formulation isotonic. Examples of such isotonic agents include glycerol, arabitol, xylitol, adonitol, mannitol, sorbitol, dulcitol, and like polyhydric alcohols; methanol, ethanol, isopropyl alcohol, and like monohydric alcohols; arabinose, xylose, ribose, 2-deoxyribose, glucose, fructose, galactose, mannose, sorbose, rhamnose, fucose, and like monosaccharides; sucrose, maltose, lactose, cellobiose, trehalose, and like disaccharides; maltotriose, raffinose, stachyose, and like oligosaccharides; glycine, leucine, arginine, and like amino acids; or derivatives thereof.

These isotonic agents may be used singly or in a combination of two or more.

The amount of isotonic agent is not limited as long as it is acceptable for use in an injectable formulation, and may be adjusted to an amount sufficient for making the injectable aqueous suspension formulation isotonic with body fluids. The amount is typically 0.1 to 20 parts by weight, preferably 0.5 to 15 parts by weight, per 100 parts by weight of water for injection contained in the injectable formulation of the invention.

(c) pH Adjusting Agent

The injectable aqueous suspension formulation may optionally contain a pH adjusting agent, which may be used in an amount effective for adjusting the pH of the aqueous suspension to within the range of about 2 to 12, and preferably about 7.

The pH adjusting agent may be an acid or base, depending on whether the pH of the injectable aqueous suspension formulation needs to be raised or lowered to reach the desired neutral pH of about 7.

When the pH needs to be lowered, suitable pH adjusting agents may be, for example, hydrochloric acid, acetic acid, and like acidic pH adjusting agents; among which hydrochloric acid is preferred.

When the pH needs to be raised, suitable pH adjusting agents may be, for example, sodium hydroxide, potassium hydroxide, calcium carbonate, magnesium oxide, magnesium hydroxide, and like basic pH adjusting agents; among which sodium hydroxide is preferred.

The injectable aqueous suspension formulation of the invention is used to treat schizophrenia and related disorders such as bipolar disorder and dementia in human patients. The injectable formulation is administered in a single injection or multiple injections, wherein after one administration, another readministration is basically not required for at least one month. The injectable formulation is preferably administered intramuscularly, although subcutaneous injections are acceptable as well. The dose of the injectable aqueous suspension formulation per administration is about 0.1 to 5 ml, and preferably about 0.5 to 3 ml.

Thus, the present invention provides a method for treating schizophrenia, comprising administering an injectable aqueous suspension formulation to a patient in need of such treatment. The present invention also provides use of an injectable aqueous suspension formulation for production of a medicament for treating schizophrenia. The present invention further provides an injectable aqueous suspension formulation for use in treating schizophrenia.

EXAMPLES

The present invention will be described in more detail below with reference to Examples, Reference Examples, Comparative Examples and Test Examples. In the Examples, Reference Examples, Comparative Examples and Test Examples "%" means "wt. %" unless otherwise specified.

In the Examples, Reference Examples and Comparative Examples, physical properties were measured according to the following methods.

Molecular Weight of Biodegradable Polymer

The molecular weight of the biodegradable polymer is the polystyrene-equivalent number average molecular weight measured by gel permeation chromatography (GPC) using polystyrene as a standard.

Mean Particle Size of Microspheres

Mean particle size was measured with a Laser Diffraction Particle Size Analyzer (SALD-3000J, manufactured by Shimadzu Corp.). In the following examples, the measured mean particle sizes of the microspheres obtained all fell within a range of 20 to 150 μm.

Aripiprazole Content of Microspheres

Microspheres were dissolved in acetone and filled up with an HPLC mobile phase, and the amount of aripiprazole was measured by HPLC. The mobile phase was prepared by dissolving 1.59 g of anhydrous sodium sulfate in 560 mL of water, and mixing the solution with 330 mL of acetonitrile and 110 mL of methanol.

Average Thickness of Shell

The microspheres were embedded in paraffin and cut on a sliding microtome (SM2000R, manufactured by LEICA) for observation under an electron microscope. The thickness was measured at five arbitrary places of the shell in an electron microscope image to calculate the average value as the average thickness of the shell.

Example 1

(i) Aripiprazole hydrate (100 mg) and about 66 mg of polylactic acid (molecular weight: 20,000) were dissolved in 2 mL of dichloromethane.

(ii) The dichloromethane solution was added to 20 mL of a 1% polyvinyl alcohol (PVA) aqueous solution while being cooled with ice, and the mixture was emulsified with a homogenizer (tradename: Polytron Homogenizer PT3000, manufactured by KINEMATICA) at 2000 rpm for 1 minute to obtain an O/W emulsion.

The resulting O/W emulsion was added to 80 mL of a 1% PVA aqueous solution (about 10° C.) stirred at 400 rpm to obtain an O/W emulsion.

(iii) The obtained O/W emulsion (about 10° C.) was placed in a 200 mL glass beaker. The glass beaker was placed in an open system at room temperature and the emulsion was stirred overnight. As a result, precipitation of particles was confirmed.

Subsequently, filtration with a 10 μm filter was carried out, and particles on the filter were air-dried to obtain dry particles. The mean particle size of the resulting particles (microspheres of the present invention) was 38.0 μm and the aripiprazole content of the microspheres was 57.8%.

Example 2

Aripiprazole hydrate (100 mg) and about 25 mg of polylactic acid (molecular weight: about 100,000) were dissolved in 2 mL of dichloromethane. The dichloromethane solution was added to 100 mL of a 1% PVA aqueous solution (about 10° C.) stirred at 400 rpm to obtain an O/W emulsion. The obtained O/W emulsion (about 10° C.) was placed in a 200 mL glass beaker. The glass beaker was placed in an open system at room temperature and the emulsion was stirred overnight.

Subsequently, filtration with a 10 μm filter was carried out, and particles on the filter were air-dried to obtain dry particles (microspheres of the present invention). The aripiprazole content of the resulting microspheres was 72.7%.

Figure 4:
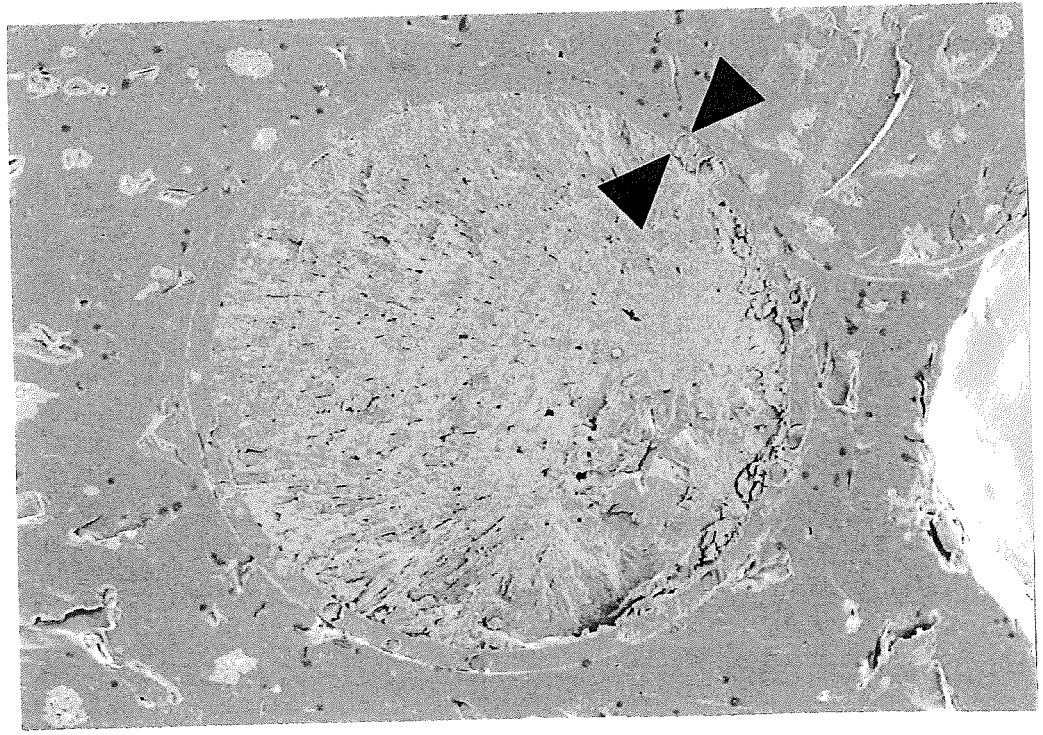
FIG. 4 is an electron microscope image of the entire cut surface of the microsphere obtained in Example 2, wherein the layer between two triangles (▲) is the shell.
Figure 5:
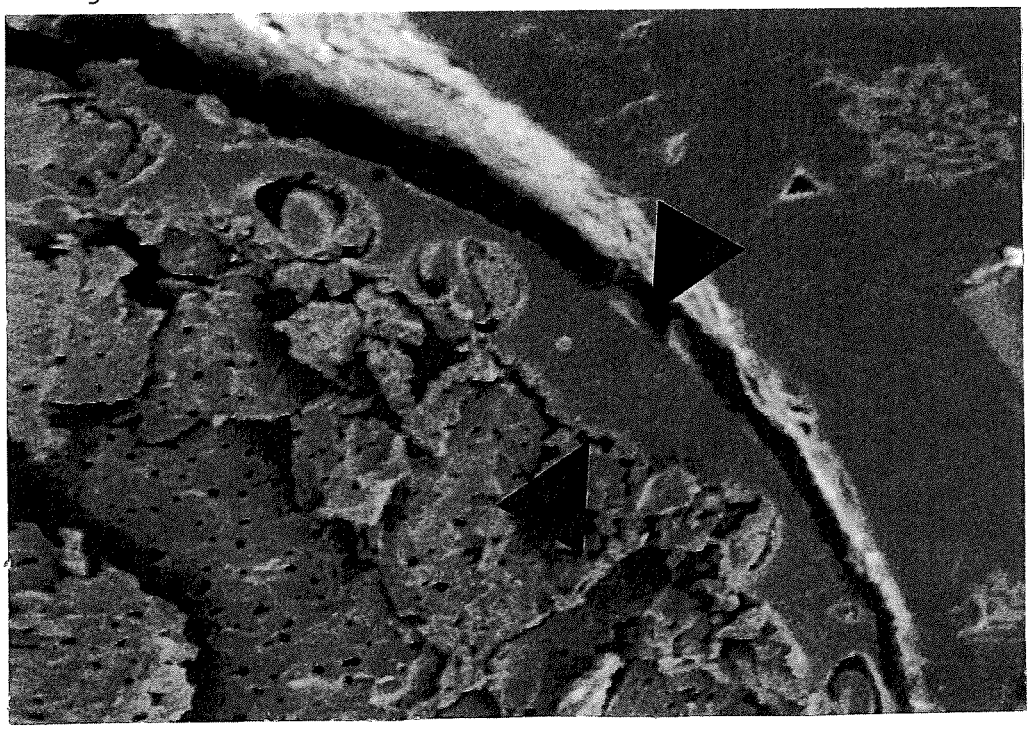
FIG. 5 shows an enlarged electron microscope image of a part of the cut surface of the microsphere obtained in Example 2, wherein the layer between two triangles (▲) is the shell.

In order to observe the inside of the particles, the obtained microspheres were embedded in paraffin and cut on a sliding microtome for observation under an electron microscope. The obtained electron microscope images are shown in FIGS. 4 and 5. As a result, a layer (shell) with a thickness of several μm was observed on the surface. In FIGS. 4 and 5, the distance between two triangles (▲) indicates the thickness of the shell.

Example 3

Aripiprazole hydrate (100 mg) and about 66 mg of polylactic acid (molecular weight: about 100,000) were dissolved in 2 mL of dichloromethane. The dichloromethane solution was added to 100 mL of a 1% PVA aqueous solution (about 10° C.) stirred at 400 rpm to obtain an O/W emulsion. The obtained O/W emulsion (about 10° C.) was placed in a 200 mL glass beaker. The glass beaker was placed in an open system at room temperature and the emulsion was stirred overnight.

Subsequently, filtration with a 10 μm filter was carried out, and particles on the filter were air-dried to obtain dry particles (microspheres of the present invention). The aripiprazole content of the resulting microspheres was 56.9%.

Example 4

Aripiprazole hydrate (100 mg) and about 11 mg of polylactic acid (molecular weight: about 100,000) were dissolved in 2 mL of dichloromethane. The dichloromethane solution was added to 100 mL of a 1% PVA aqueous solution (about 10° C.) stirred at 400 rpm to obtain an O/W emulsion. The obtained O/W emulsion (about 10° C.) was placed in a glass beaker. The glass beaker was placed in an open system at room temperature and the emulsion was stirred overnight.

Subsequently, filtration with a 10 μm filter was carried out, and particles on the filter were air-dried to obtain dry particles (microspheres of the present invention). The aripiprazole content of the resulting microspheres was 89.6%.

Example 5

Aripiprazole hydrate (100 mg) and about 25 mg of polylactic acid (molecular weight: about 100,000) were dissolved in 2 mL of dichloromethane. The dichloromethane solution was added to 20 mL of a 1% PVA aqueous solution while being cooled with ice, and the mixture was stirred with a Polytron Homogenizer at 2000 rpm for 1 minute. The resulting liquid was added to 80 mL of a 1% PVA solution (about 10° C.) stirred at 400 rpm to obtain an O/W emulsion. The obtained O/W emulsion (about 10° C.) was placed in a 200 mL glass beaker. The glass beaker was placed in an open system at room temperature and the emulsion was stirred overnight.

Subsequently, filtration with a 10 μm filter was carried out, and particles on the filter were air-dried to obtain dry particles (microspheres of the present invention). The mean particle size of the resulting particles was 64.9 μm and the aripiprazole content of the microspheres was 79.7%.

An electron microscope image of the resulting particles is shown in FIG. 1. As is clear from FIG. 1, the obtained particles (microspheres of the invention) are spherical.

Figure 6:
FIG. 6 is an electron microscope image of the entire cut surface of the microsphere obtained in Example 5, wherein the layer between two triangles (▲) is the shell.
Figure 7:
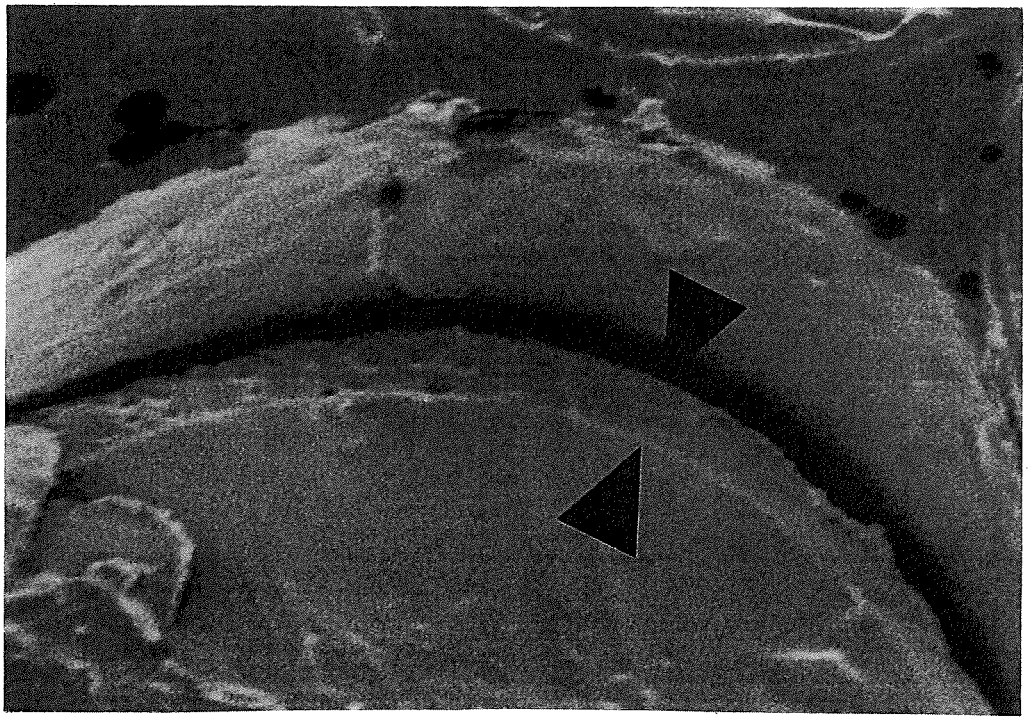
FIG. 7 shows an enlarged electron microscope image of a part of the cut surface of the microsphere obtained in Example 5, wherein the layer between two triangles (▲) is the shell.

Next, in order to observe the inside of the particles, the obtained microspheres were embedded in paraffin and cut on a sliding microtome for observation under an electron microscope. Electron microscope images are shown in FIGS. 6 and 7. Consequently, as shown in FIGS. 6 and 7, a layer (shell) with a thickness of several μm was observed on the surface. In FIGS. 6 and 7, the distance between two triangles (▲) indicates the thickness of the shell.

Figure 8:
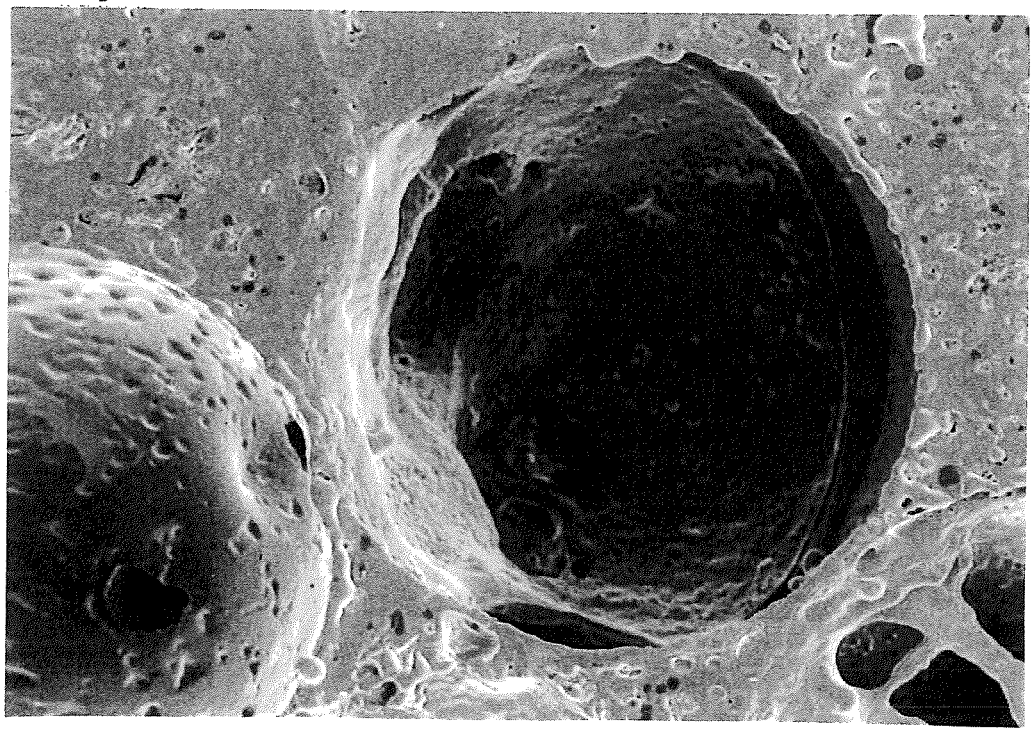
FIG. 8 is an electron microscope image of the cut surface of the microsphere obtained in Example 5, which was cut, immersed in an acetic acid solution (20%), washed and dried.

Further, the cut particles were immersed for 1 hour in an acetic acid solution (20%) that does not dissolve polylactic acid but dissolves only aripiprazole, washed with purified water, and observed under an electron microscope. Electron microscope image is shown in FIG. 8. Consequently, as is clear from FIG. 8, only the core was dissolved and the shell was not dissolved. This revealed that in the microsphere of the present invention, the shell consists essentially of polylactic acid and the core consists essentially of aripiprazole.

Example 6

Aripiprazole hydrate (100 mg) and about 25 mg of polylactic acid (molecular weight: about 100,000) were dissolved in 2 mL of dichloromethane. The dichloromethane solution was added to 20 mL of a 1% PVA aqueous solution while being cooled with ice, and the mixture was stirred with a Polytron Homogenizer at 2000 rpm for 1 minute. The resulting liquid was added to 80 mL of a 1% PVA aqueous solution (about 10° C.) stirred at 400 rpm to obtain an O/W emulsion. The obtained O/W emulsion (about 10° C.) was placed in a 200 mL glass beaker. The glass beaker was placed in an open system at room temperature and the emulsion was stirred for 4 hours.

Subsequently, filtration with a 10 μm filter was carried out, and particles on the filter were air-dried to obtain dry particles. The mean particle size of the resulting particles was 55.1 μm.

Figure 2:
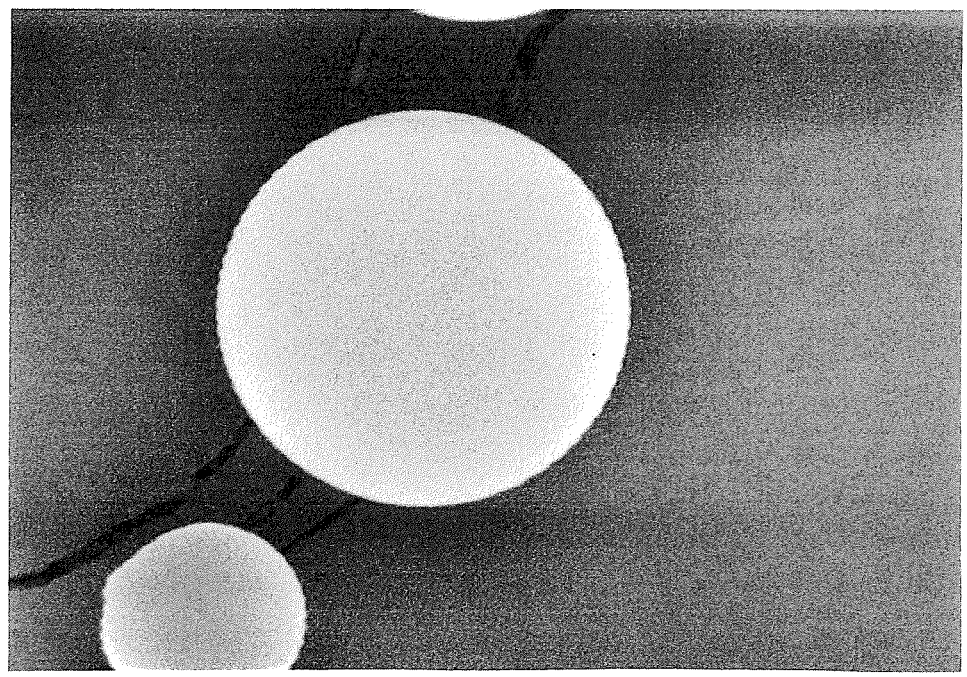
FIG. 2 is an electron microscope image of the microspheres obtained in Example 6.

An electron microscope image of the resulting particles is shown in FIG. 2. As is clear from FIG. 2, the particles (microspheres of the invention) were spherical.

Example 7

Aripiprazole hydrate (400 mg) and about 125 mg of polylactic acid (molecular weight: about 100,000) were dissolved in 10 mL of dichloromethane. The dichloromethane solution was passed through a shirasu porous glass filter with a pore size of 10 μm at 25 mL/min, and mixed with 500 mL of a 1% PVA aqueous solution (about 10° C.) to prepare an O/W emulsion. The obtained O/W emulsion (about 10° C.) was placed in a 1 L glass beaker. The glass beaker was placed in an open system at room temperature and the emulsion was stirred at 400 rpm for 4 hours.

Subsequently, filtration with a 10 μm filter was carried out, and particles on the filter were air-dried to obtain dry particles. The mean particle size of the resulting particles (microspheres of the invention) was 78.4 μm.

Example 8

Aripiprazole hydrate (400 mg) and about 125 mg of polylactic acid (molecular weight: 100,000) were dissolved in 10 mL of dichloromethane. The dichloromethane solution was passed through a shirasu porous glass filter with a pore size of 20 μm at 25 mL/min, and mixed with 500 mL of a 1% PVA aqueous solution (about 10° C.) to prepare an O/W emulsion. The obtained O/W emulsion (about 10° C.) was placed in a 1 L glass beaker. The glass beaker was placed in an open system at room temperature and the emulsion was stirred at 400 rpm for 4 hours.

Subsequently, filtration with a 10 μm filter was carried out, and particles on the filter were air-dried to obtain dry particles. The mean particle size of the resulting particles (microspheres of the invention) was 129.3 μm.

Example 9

Aripiprazole hydrate (400 mg) and about 125 mg of polylactic acid (molecular weight: 100,000) were dissolved in 10 mL of dichloromethane. The dichloromethane solution was passed through a shirasu porous glass filter with a pore size of 15 μm at 25 mL/min, and mixed with 500 mL of a 1% PVA aqueous solution (about 10° C.) to prepare an O/W emulsion. The obtained O/W emulsion (about 10° C.) was placed in a 1 L glass beaker. The glass beaker was placed in an open system at room temperature and the emulsion was stirred at 400 rpm for 4 hours.

Subsequently, filtration with a 10 μm filter was carried out, and particles on the filter were air-dried to obtain dry particles. The mean particle size of the resulting particles (microspheres of the invention) was 125.5 μm.

Example 10

Aripiprazole hydrate (400 mg) and about 125 mg of a lactic acid-glycolic acid copolymer (lactic acid/glycolic acid=75/25 (molar ratio), molecular weight: about 63,800) were dissolved in 10 mL of dichloromethane. The dichloromethane solution was passed through a shirasu porous glass filter with a pore size of 10 μm at 25 mL/min, and mixed with 500 mL of a 1% PVA aqueous solution (about 10° C.) to prepare an O/W emulsion. The obtained O/W emulsion (about 10° C.) was placed in a 1 L glass beaker. The glass beaker was placed in an open system at room temperature and the emulsion was stirred at 400 rpm for 3 hours.

Subsequently, filtration with a 10 μm filter was carried out, and particles on the filter were vacuum-dried at 40° C. to obtain dry particles. The mean particle size of the resulting particles (microspheres of the invention) was 69.3 μm and the aripiprazole content of the microspheres was 72.0%.

Example 11

Aripiprazole hydrate (500 mg) and about 125 mg of a lactic acid-glycolic acid copolymer (lactic acid/glycolic acid=75/25 (molar ratio), molecular weight: about 63,800) were dissolved in 10 mL of dichloromethane. The dichloromethane solution was passed through a shirasu porous glass filter with a pore size of 10 μm at 25 mL/min, and mixed with 500 mL of a 1% PVA aqueous solution (about 10° C.) to prepare an O/W emulsion. The O/W emulsion (about 10° C.) was placed in a 1 L glass beaker. The glass beaker was placed in an open system at room temperature and the emulsion was stirred at 400 rpm for 3 hours.

Subsequently, filtration with a 10 μm filter was carried out, and particles on the filter were vacuum-dried at 40° C. and sieved with a 150 μm sieve to obtain dry particles. The mean particle size of the resulting particles (microspheres of the invention) was 85.5 μm and the aripiprazole content of the microspheres was 75.2%.

Example 12

Aripiprazole hydrate (500 mg) and about 125 mg of polylactic acid (molecular weight: 100,000) were dissolved in 10 mL of dichloromethane. The dichloromethane solution was passed through a shirasu porous glass filter with a pore size of 10 μm at 25 mL/min, and mixed with 500 mL of a 1% PVA aqueous solution (about 10° C.) to prepare an O/W emulsion. The obtained O/W emulsion (about 10° C.) was placed in a 1 L glass beaker. The glass beaker was then placed in an open system at room temperature, and the emulsion was stirred at 400 rpm for 3 hours.

Subsequently, filtration with a 10 μm filter was carried out, and particles on the filter were vacuum-dried at 40° C. to obtain dry particles. The mean particle size of the resulting particles (microspheres of the invention) was 89.2 μm and the aripiprazole content of the microspheres was 75.8%.

Example 13

Aripiprazole hydrate (500 mg) and about 125 mg of polylactic acid (molecular weight: 100,000) were dissolved in 10 mL of dichloromethane. The dichloromethane solution was passed through a shirasu porous glass filter with a pore size of 10 μm at 25 mL/min, and mixed with 500 mL of a 1% PVA aqueous solution (about 10° C.) to prepare an O/W emulsion. The obtained O/W emulsion (about 10° C.) was placed in a 1 L glass beaker. The glass beaker was placed in an open system at room temperature and the emulsion was stirred at 400 rpm for 3 hours at room temperature.

Subsequently, filtration with a 10 μm filter was carried out, and particles on the filter were vacuum-dried at 40° C. and sieved with a 150 μm sieve to obtain dry particles. The mean particle size of the resulting particles (microspheres of the invention) was 78.1 μm and the aripiprazole content of the microspheres was 75.6%.

Reference Example 1

Aripiprazole hydrate (100 mg) was dissolved in 2 mL of dichloromethane, and the solution was added dropwise to 100 mL of a 1% PVA aqueous solution (about 10° C.) stirred at 400 rpm to obtain an O/W emulsion (about 10° C.). The obtained O/W emulsion (about 10° C.) was placed in a 200 mL glass beaker. The beaker was placed in an open system at room temperature, and the emulsion was stirred overnight.

Figure 3:
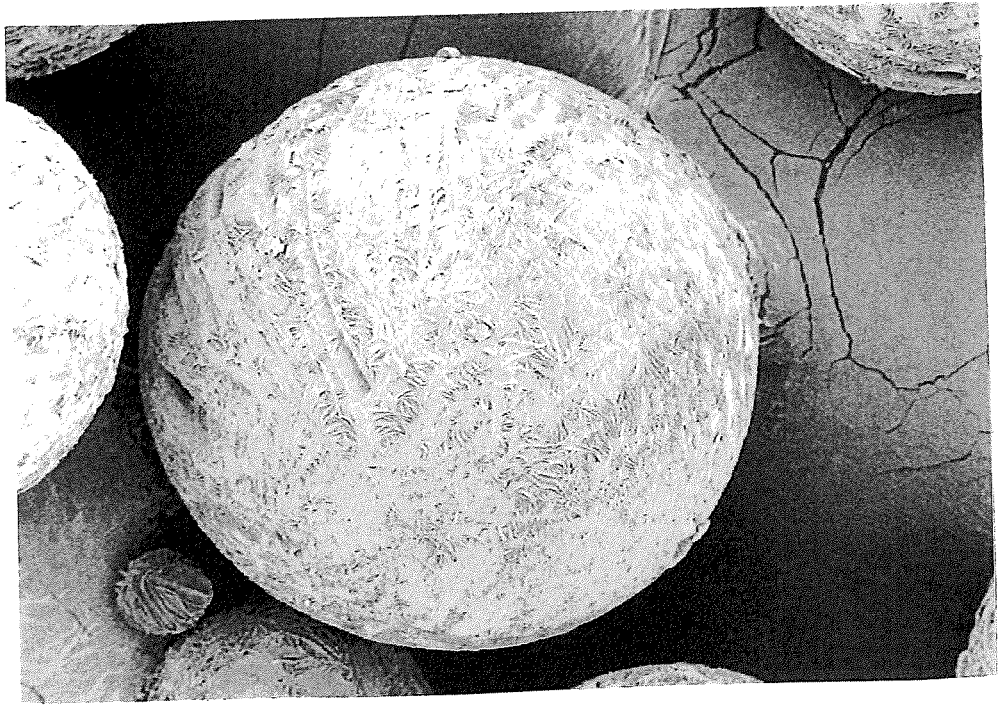
FIG. 3 is an electron microscope image of the aripiprazole spherical particles obtained in Reference Example 1.

Subsequently, filtration with a 10 μm filter was carried out, and particles on the filter were air-dried to obtain dry particles. An electron microscope image of the obtained particles is shown in FIG. 3. As is clear from FIG. 3, the aripiprazole particles were spherical.

Test Example 1

According to the Japanese Pharmacopoeia, a dissolution test was conducted using the paddle method. Specifically, about 50 mg of the microspheres of Examples 5 and 6, calculated as aripiprazole anhydride, were measured out, and added to 900 mL of a 0.5% sodium dodecyl sulfate aqueous solution to conduct the dissolution test using the paddle method at 100 rpm.

Figure 9:
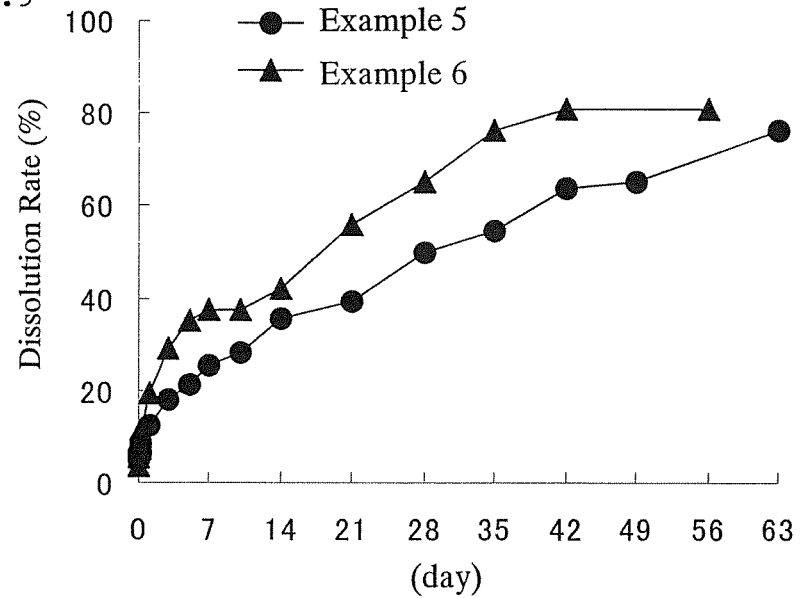
FIG. 9 is a graph that shows the results of the dissolution test of the microspheres obtained in Examples 5 and 6.

The results are shown in FIG. 9. As is clear from FIG. 9, the microspheres of Examples 5 and 6 show dissolution for at least two months.

Test Example 2

The microspheres were administered to rabbits, and the blood concentration of aripiprazole was measured. More specifically, the lactic acid-glycolic acid copolymer (PLGA) microspheres (PLGA MS, hereinafter) obtained in Example 11 and the polylactic acid (PLA) microspheres (PLA MS, hereinafter) obtained in Example 13 were dispersed separately in a 1.5% aqueous sodium carboxymethylcellulose solution containing 0.75% sodium chloride such that the aripiprazole content became 10% (W/V).

The obtained suspension was injected subcutaneously into the posterior cervical region of each rabbit in such a manner that the dose of the aripiprazole was 25 mg/kg. Blood samples of the rabbit were collected for 84 days after the administration. The aripiprazole blood concentration (mean and standard deviation (S.D.)) was measured. Table 1 shows the results for "PLA MS" and Table 2 shows the results for "PLGA MS".

TABLE 1

PLA MS n = 4

| Example 13 | | Time (day) | | | | | | | | | | | |
|---|---|---|---|---|---|---|---|---|---|---|---|---|---|
| | | 0 | 1 | 3 | 7 | 14 | 21 | 28 | 35 | 42 | 49 | 56 | 70 | 84 |
| Plasma Concentration (ng/mL) | Mean | 0.00 | 1.91 | 1.22 | 2.40 | 3.70 | 3.82 | 5.21 | 6.25 | 4.69 | 4.59 | 4.46 | 4.77 | 4.02 |
| | S.D. | 0.00 | 0.97 | 0.61 | 0.97 | 2.1 | 1.27 | 1.93 | 2.14 | 0.82 | 0.46 | 0.93 | 1.6 | 1.01 |

TABLE 2

PLGA MS n = 4

| Example 11 | | Time (day) | | | | | | | | | | | |
|---|---|---|---|---|---|---|---|---|---|---|---|---|---|
| | | 0 | 1 | 3 | 7 | 14 | 21 | 28 | 35 | 42 | 49 | 56 | 70 | 84 |
| Plasma Concentration (ng/mL) | Mean | 0.00 | 1.25 | 1.02 | 2.29 | 6.21 | 5.96 | 7.29 | 9.01 | 7.27 | 7.83 | 8.54 | 5.52 | 4.42 |
| | S.D. | 0.00 | 0.31 | 0.36 | 1.23 | 1.66 | 3.74 | 1.99 | 1.38 | 2.36 | 0.89 | 2.75 | 0.81 | 0.38 |

Figure 10:
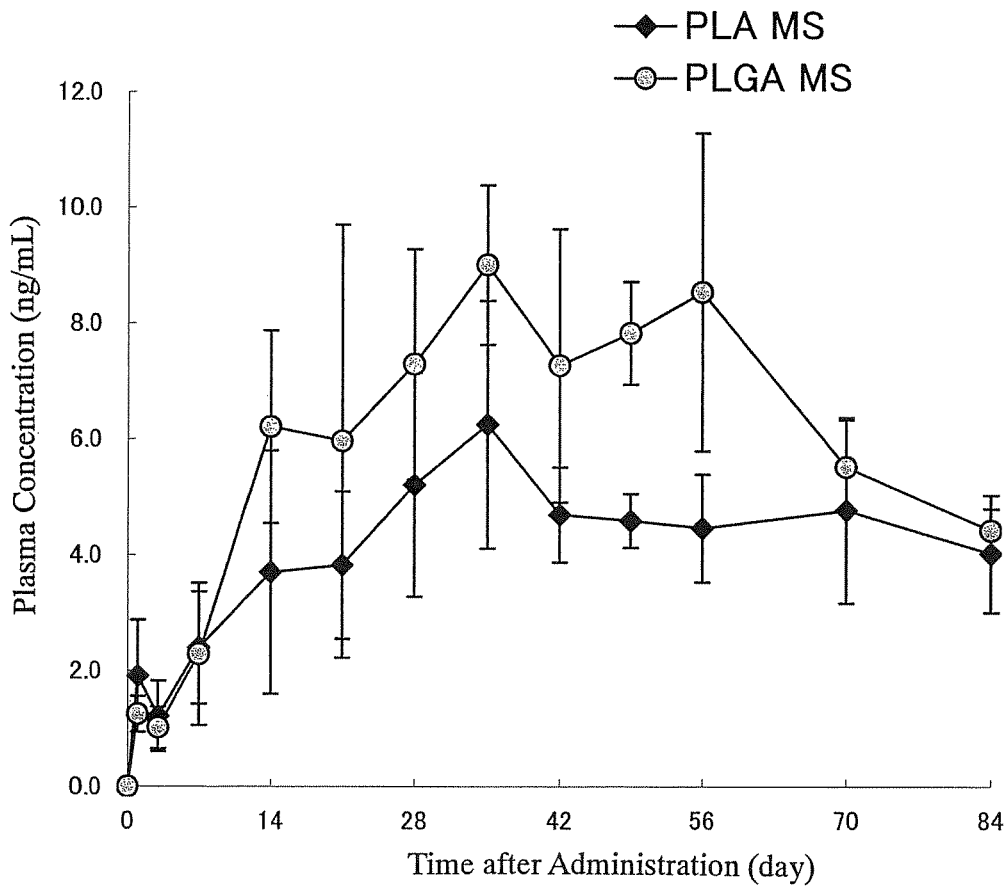
FIG. 10 is a graph that shows the results of Tables 1 and 2, regarding Test Example 2.

FIG. 10 shows a graph of the data of Tables 1 and 2.

As shown in FIG. 10, the aripiprazole concentration in rabbit blood was consistently high throughout the 84 days. The blood concentration did not decrease on Day 84, and it is presumed that the blood concentration will remain at a high level for three months or longer.

Comparative Example 1

Aripiprazole hydrate (about 100 mg) and about 66 mg of a lactic acid-glycolic acid copolymer (lactic acid/glycolic acid=50/50 (molar ratio), molecular weight: about 20,000) were dissolved in 2 mL of dichloromethane. The dichloromethane solution was added to 100 mL of a 1% polyvinyl alcohol (PVA) aqueous solution (23° C.) stirred at 400 rpm to prepare an O/W emulsion (about 23° C.).

The obtained O/W emulsion (about 23° C.) was placed in a glass beaker. The glass beaker was placed in an open system at room temperature and the emulsion was stirred at 400 rpm for 32 hours.

Subsequently, filtration with a 10 μm filter was carried out, and particles on the filter were air-dried to obtain dry particles.

Figure 11:
FIG. 11 is an electron microscope image of the particles obtained in Comparative Example 1.

As shown in FIG. 11, the resulting particles had irregular shapes, such as plates, etc. The method thus failed to obtain spherical microspheres.

Comparative Example 2

Aripiprazole hydrate (about 190 mg) and about 1.2 g of a lactic acid-glycolic acid copolymer (lactic acid/glycolic acid=50/50 (molar ratio), molecular weight: about 20,000) were dissolved in 4 mL of dichloromethane. The dichloromethane solution was added to 100 mL of a 1% polyvinyl alcohol (PVA) aqueous solution (23° C.), and the mixture was homogenized for a minute at 2000 rpm using a homogenizer (product name: Polytron Homogenizer PT3000, produced by Kinematica) to prepare an O/W emulsion (about 23° C.). The obtained O/W emulsion (about 23° C.) was added to 900 mL of a 1% PVA aqueous solution (about 23° C.) stirred at 400 rpm. The resulting mixture was placed in a glass beaker. The glass beaker was placed in an open system at room temperature, and the mixture therein was stirred for 32 hours.

Subsequently, filtration with a 10 μm filter was carried out, and particles on the filter were air-dried to obtain dry particles.

Figure 12:
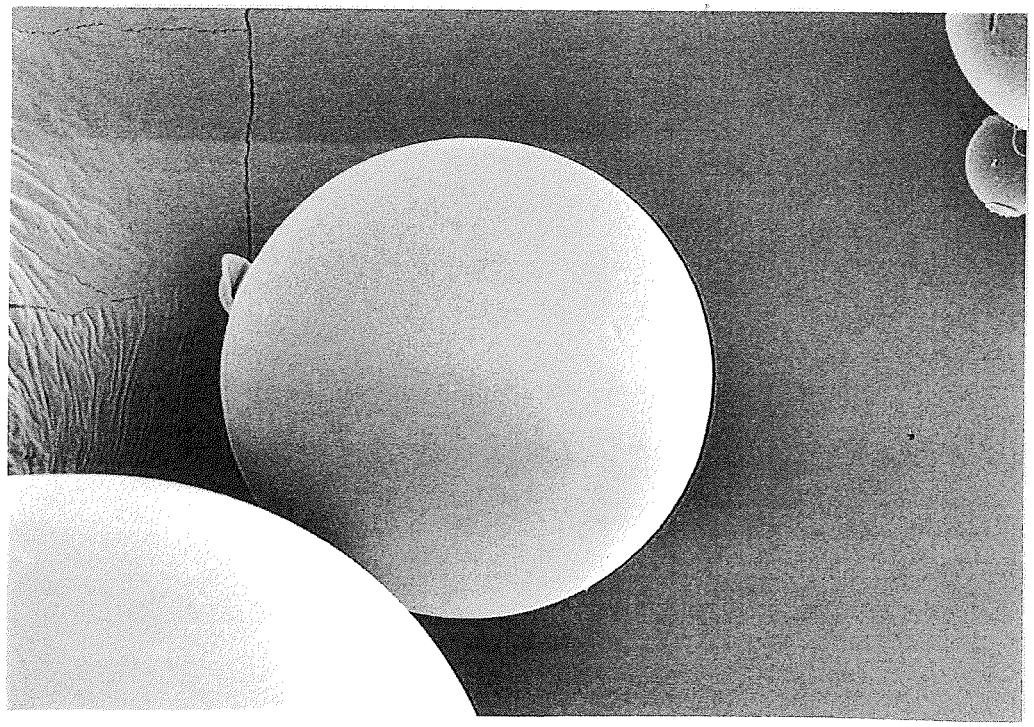
FIG. 12 is an electron microscope image of the particles obtained in Comparative Example 2.
Figure 13:
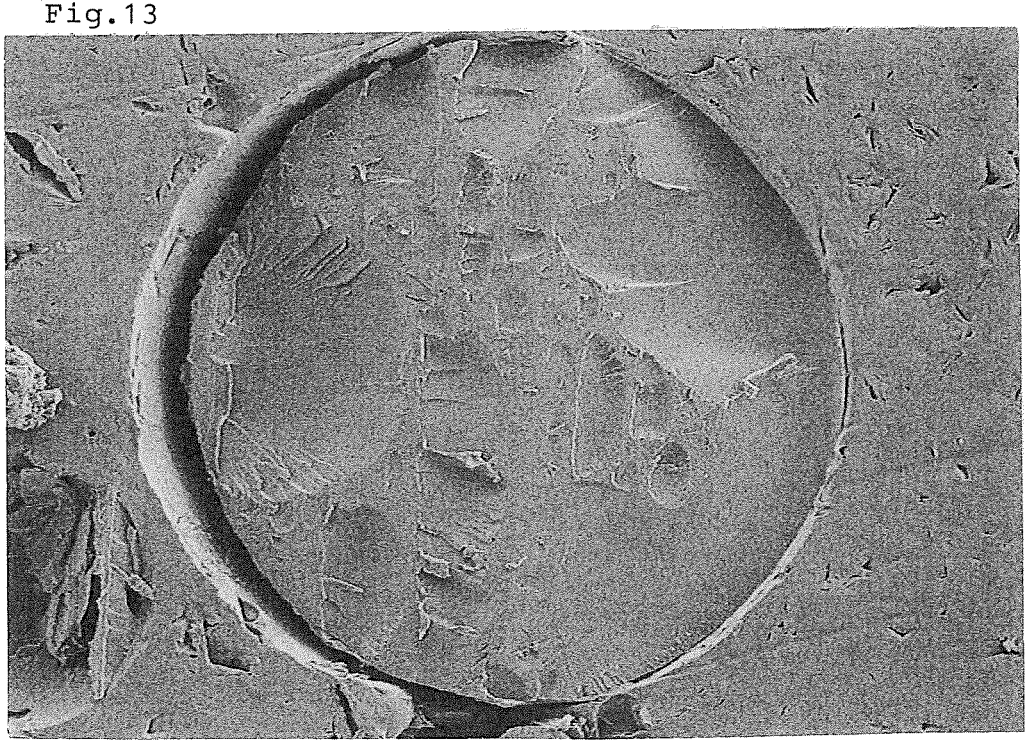
FIG. 13 is an electron microscope image of the entire cut surface of a particle obtained in Comparative Example 2.
Figure 14:
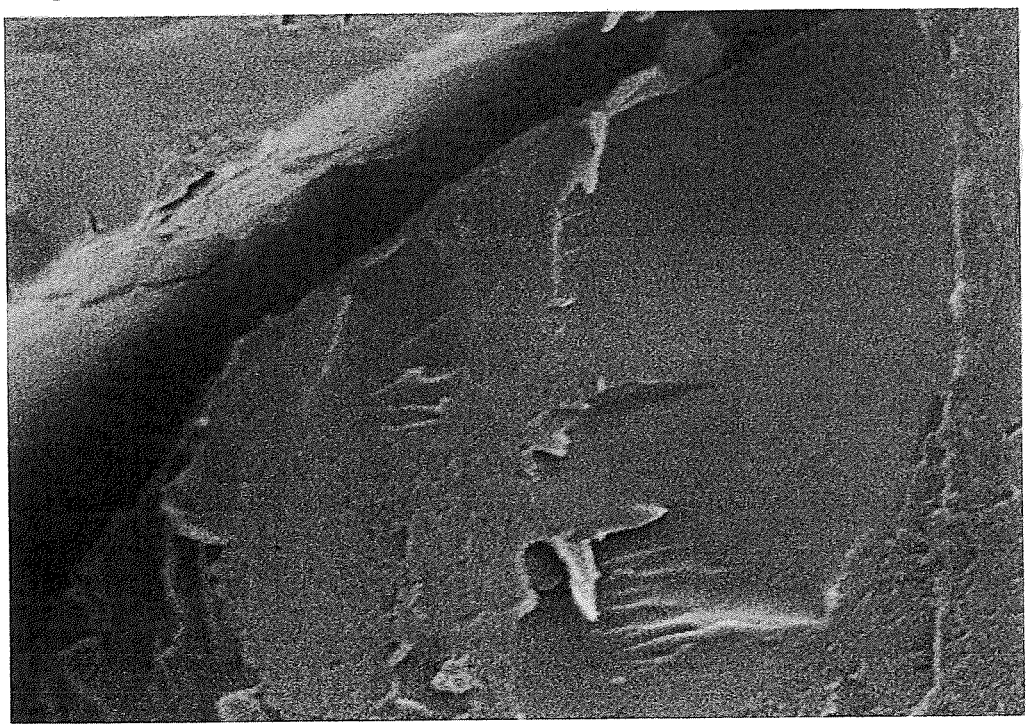
FIG. 14 shows an enlarged electron microscope image of a part of the cut surface of the particle obtained in Comparative Example 2.

As shown in FIG. 12, the obtained particles were spherical. The microspheres were then embedded in paraffin and cut with a sliding microtome. The cut particles were observed with an electron microscope, as shown in FIGS. 13 and 14. In those particles, a core/shell structure was not observed, as is clear from comparison with FIGS. 6 and 7. The above method thus failed to obtain microspheres having a core/shell structure.

INDUSTRIAL APPLICABILITY

The microspheres having a core/shell structure of the present invention have a high aripiprazole content, and accordingly administration of even a small amount of particles (microspheres) allows for the administration of a high dose of aripiprazole. Further, microspheres having a core/shell structure of the invention have excellent sustained-release properties, since a core containing aripiprazole is coated with a shell made of a biodegradable polymer. Moreover, the microspheres of the invention are spherical and hence have excellent flowability during filling in the production of an injectable formulation, and excellent syringeability during administration of the injectable formulation.

The invention claimed is:

1. Microspheres having a core/shell structure and a spherical shape,
   (a) the core comprising solid-state aripiprazole, wherein the solid-state aripiprazole is from a form chosen from aripiprazole hydrate, anhydrous crystal B, anhydrous crystal C, anhydrous crystal D, anhydrous crystal E, anhydrous crystal F, anhydrous crystal G, and two or more combinations thereof, and wherein the core has a spherical shape; and
   (b) the shell coating from 80% to 100% of the surface of the core, and the shell comprising a biodegradable polymer,
   wherein:
   the aripiprazole content is 55 to 95% by weight of the total weight of the microsphere and the microspheres have a mean particle size of 20 to 150 μm,
   the shell has an average thickness of 0.5 to 20 μm,
   the biodegradable polymer is at least one member selected from the group consisting of polylactic acids and lactic acid-glycolic acid copolymers, and
   the polylactic acids or the lactic acid-glycolic acid copolymers have a molecular weight of 5,000 to 200,000.

2. An injectable aqueous suspension formulation comprising:
   microspheres having a core/shell structure and a spherical shape,
   (a) the core comprising solid-state aripiprazole, wherein the solid-state aripiprazole is from a form chosen from aripiprazole hydrate, anhydrous crystal B, anhydrous crystal C, anhydrous crystal D, anhydrous crystal E, anhydrous crystal F, anhydrous crystal G, and two or more combinations thereof, and wherein the core has a spherical shape; and
   (b) the shell coating from 80% to 100% of the surface of the core, and the shell comprising a biodegradable polymer,
   wherein:
   the aripiprazole content is 55 to 95% by weight of the total weight of the microsphere and the microspheres have a mean particle size of 20 to 150 μm,
   the shell has an average thickness of 0.5 to 20 μm,
   the biodegradable polymer is at least one member selected from the group consisting of polylactic acids and lactic acid-glycolic acid copolymers, and
   the polylactic acids or the lactic acid-glycolic acid copolymers have a molecular weight of 5,000 to 200,000,
   a vehicle therefor, and
   water for injection.

3. The formulation according to claim 2, wherein upon injection, releases aripiprazole over a period of at least one month.

4. An injectable aqueous suspension formulation according to claim 2 or 3, wherein the vehicle comprises:
   (1) one or more suspending agents,
   (2) one or more isotonic agents, and
   (3) optionally one or more pH adjusting agents.

5. A process for producing microspheres having a core/shell structure and a spherical shape according to claim 1, the process comprising:
   (i) preparing a solution containing aripiprazole, a biodegradable polymer, and an organic solvent;
   (ii) mixing the solution obtained in step (i) with water to obtain an O/W emulsion, under temperature conditions that do not allow freezing of the organic solvent and water and that suppress evaporation of the organic solvent; and (iii) removing the organic solvent at least partially from the O/W emulsion under conditions effective for allowing the aripiprazole to precipitate in the form of spherical particles.

6. A process according to claim 5, wherein the organic solvent used in step (i) is a water-immiscible organic solvent.

7. A process according to claim 5, wherein the water used in step (ii) contains an emulsifier.

8. A process according to claim 5, wherein step (ii) comprises the substeps of (a) dispersing the solution obtained in step (i) in water in the presence or absence of an emulsifier to form an O/W emulsion and (b) dispersing the O/W emulsion obtained in substep (a) in water in the presence or absence of an emulsifier to form an O/W emulsion.

9. A process according to claim 5, wherein, in step (ii), the O/W emulsion is produced under low-temperature conditions effective for suppressing evaporation of the organic solvent, and in step (iii), the low temperature emulsion obtained in step (ii) is stirred in an open system at room temperature to allow the organic solvent to volatilize.

10. A method for treating schizophrenia, comprising administering an injectable aqueous suspension formulation according to claim 2 to a patient in need of such treatment.

11. A method for treating schizophrenia in a subject in need thereof comprising:
administering an injectable aqueous suspension formulation comprising: microspheres having a core/shell structure and a spherical shape,
(a) the core comprising solid-state aripiprazole, wherein the solid-state aripiprazole is from a form chosen from aripiprazole hydrate, anhydrous crystal B, anhydrous crystal C, anhydrous crystal D, anhydrous crystal E, anhydrous crystal F, anhydrous crystal G, and two or more combinations thereof, and wherein the core has a spherical shape; and
(b) the shell coating from 80% to 100% of the surface of the core, and the shell comprising a biodegradable polymer,
wherein
the aripiprazole content is 55 to 95% by weight of the total weight of the microsphere and the microspheres have a mean particle size of 20 to 150 μm,
the shell has an average thickness of 0.5 to 20 μm,
the biodegradable polymer is at least one member selected from the group consisting of polylactic acids and lactic acid-glycolic acid copolymers, and
the polylactic acids or the lactic acid-glycolic acid copolymers have a molecular weight of 5,000 to 200,000,
a vehicle therefor, and
water for injection.

* * * * *

UNITED STATES PATENT AND TRADEMARK OFFICE
CERTIFICATE OF CORRECTION

PATENT NO. : 10,632,079 B2
APPLICATION NO. : 12/666761
DATED : April 28, 2020
INVENTOR(S) : Shogo Hiraoka Page 1 of 1

It is certified that error appears in the above-identified patent and that said Letters Patent is hereby corrected as shown below:

On the Title Page

Item (73) "Otsuka Pharmaceuticals Co., Ltd." should read --Otsuka Pharmaceutical Co., Ltd.--

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*